(12) United States Patent
Vaisburd et al.

(10) Patent No.: US 8,175,220 B2
(45) Date of Patent: May 8, 2012

(54) METHOD AND APPARATUS FOR SHORTENING FOOTPRINT OF MULTI-MODALITY IMAGING SYSTEM

(75) Inventors: Alexander Vaisburd, Haifa (IL); Leonid Yakubovsky, Haifa (IL); Dor Perry, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 207 days.

(21) Appl. No.: 12/186,362

(22) Filed: Aug. 5, 2008

(65) Prior Publication Data

US 2010/0034350 A1    Feb. 11, 2010

(51) Int. Cl.
*G01N 23/04* (2006.01)

(52) U.S. Cl. .......................... 378/63; 378/20

(58) Field of Classification Search .......... 378/4
See application file for complete search history.

(56) References Cited

U.S. PATENT DOCUMENTS

| | | | |
|---|---|---|---|
| 6,670,614 B1 * | 12/2003 | Plut et al. | 250/363.04 |
| 6,787,777 B1 | 9/2004 | Gagnon et al. | |
| 6,941,164 B2 | 9/2005 | Hajaj et al. | |
| 7,087,903 B2 | 8/2006 | Balan et al. | |
| 2003/0058984 A1 | 3/2003 | Susami et al. | |
| 2003/0076925 A1 * | 4/2003 | DeSilets et al. | 378/63 |
| 2006/0202650 A1 | 9/2006 | Hausner et al. | |
| 2007/0014391 A1 * | 1/2007 | Mostafavi et al. | 378/63 |
| 2007/0238950 A1 | 10/2007 | Vija et al. | |
| 2008/0173218 A1 * | 7/2008 | Wang et al. | 108/20 |
| 2008/0212859 A1 * | 9/2008 | Da Silva et al. | 382/131 |

FOREIGN PATENT DOCUMENTS

JP        2006166968        6/2006

OTHER PUBLICATIONS

PCT International Search Report, International Application No. PCT/US2009/051093, Date of Mailing: Sep. 29, 2009, GEHC, U.S. Appl. No. 12/186,362, filed Aug. 5, 2008, (5) pages.

* cited by examiner

*Primary Examiner* — Hoon Song
(74) *Attorney, Agent, or Firm* — The Small Patent Law Group; Dean D. Small (57) ABSTRACT

A multi-modality imaging system includes a first imaging system and a second imaging system that is different from the first imaging system. The first and second imaging systems are slidingly mounted on at least one rail. A table has a movable pallet configured to extend through a scan range of the first imaging system while the first and second imaging systems are positioned proximate each other at one position along the at least one rail. The pallet is further configured to extend through a scan range of the second imaging system while the first and second imaging systems are positioned proximate each other at a different position along the at least one rail. At least a portion of the scan ranges overlap each other.

20 Claims, 10 Drawing Sheets

METHOD AND APPARATUS FOR SHORTENING FOOTPRINT OF MULTI-MODALITY IMAGING SYSTEM

BACKGROUND OF THE INVENTION

This invention relates generally to multi-modality imaging systems, and more particularly to shortening the footprint of the multi-modality imaging system without comprising the scanning range.

Multi-modality imaging systems employ a plurality of imaging systems, such as a Nuclear Medicine (NM) imaging system and a Computed Tomography (CT) imaging system that are aligned with respect to each other. In some applications, attenuation correction of the NM image data may be accomplished by acquiring attenuation data with the CT imaging system. The combination of the two sets of image data shows the relationship between the emission or NM image data and structural elements shown by the CT image data. The two sets of image data need to be registered with respect to each other so that the data sets may be properly combined.

The system has a patient bed that provides a pallet for supporting the patient during imaging. The pallet travels through the two modalities to move anatomy of interest into the fields of view of each of the imaging systems. The pallet length may be extended to increase the length of travel and to increase the scanning range of the modality furthest from the table. However, a larger room is needed to accommodate the extended travel length of the pallet. Another problem is that the portion of the pallet extending away from the bed may sag under the weight of the patient. This may occur even without an extended length pallet due to the weight of the patient. This sag results in misregistration of the two sets of image data as the anatomy is positioned lower or closer to the floor in the data set acquired furthest from the table.

BRIEF DESCRIPTION OF THE INVENTION

In one embodiment, a multi-modality imaging system comprises a first imaging system and a second imaging system that is different from the first imaging system. The first and second imaging systems are slidingly mounted on at least one rail. A table comprises a movable pallet configured to extend through a scan range of the first imaging system while the first and second imaging systems are positioned proximate each other at one position along the at least one rail. The pallet is further configured to extend through a scan range of the second imaging system while the first and second imaging systems are positioned proximate each other at a different position along the at least one rail. At least a portion of the scan ranges overlap each other.

In another embodiment, a method for using a multi-modality imaging system comprises positioning first and second imaging systems proximate each other along at least one rail at a location with respect to a table. The table has a pallet configured to extend through the first and second imaging systems. Image data is acquired with the first imaging system. The first and second imaging systems are positioned proximate each other at a different location along the at least one rail that is closer to the table. Image data is acquired with the second imaging system. At least a portion of the image data that is acquired by each of the first and second imaging systems is acquired at a same distance away from the table.

In yet another embodiment, a multi-modality imaging system comprises a first imaging system and a second imaging system that are different from each other. The second imaging system is mounted to the first imaging system. The first imaging system is slidingly mounted on at least one rail.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
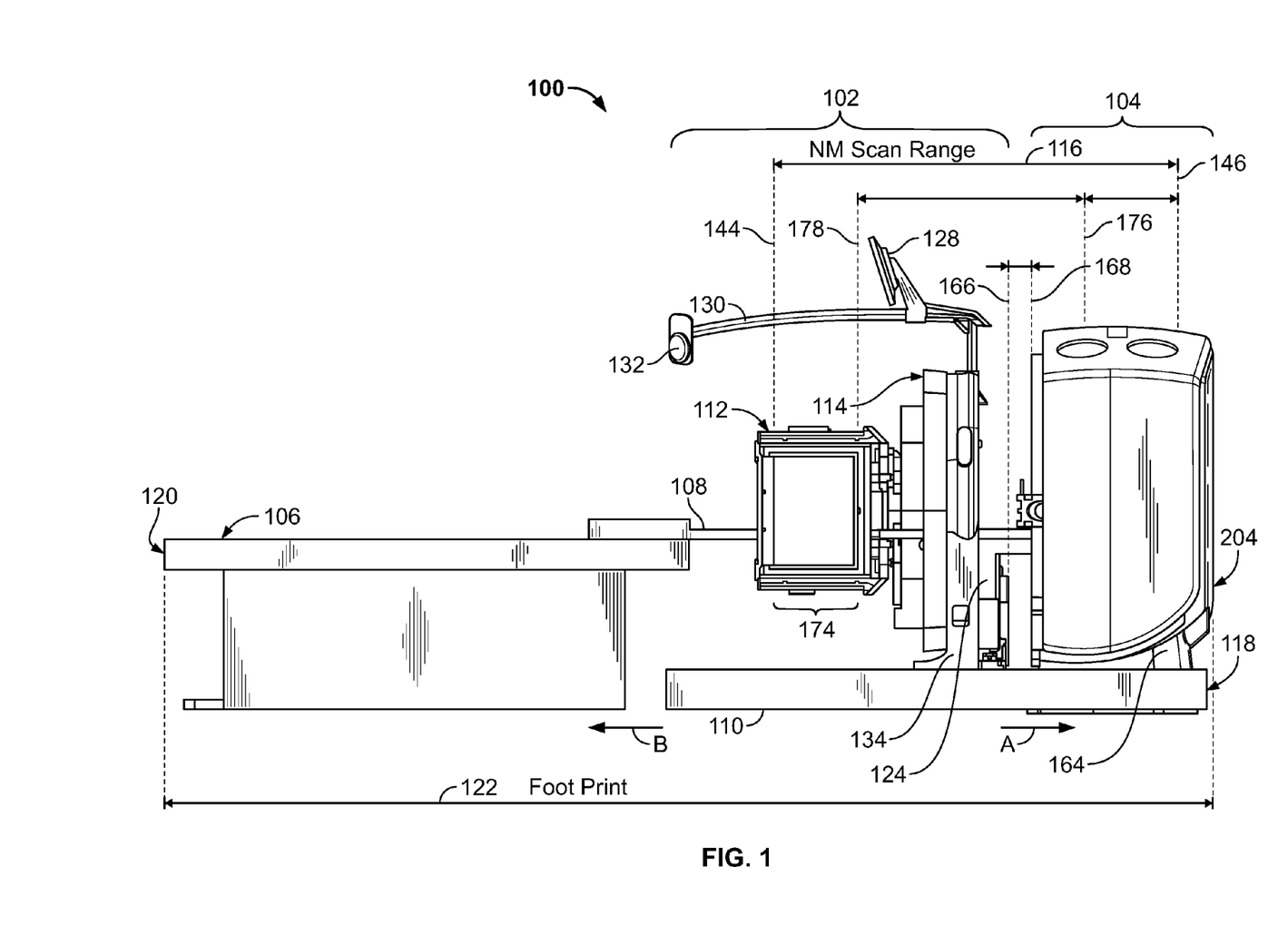
FIG. 1 illustrates a side-view of a multi-modality imaging system having a Nuclear Medicine (NM) imaging system and a computed tomography (CT) imaging system formed in accordance with an embodiment of the present invention.

FIG. 1 illustrates a side-view of a multi-modality imaging system 100 having a Nuclear Medicine (NM) imaging system 102 and a computed tomography (CT) imaging system 104. The NM imaging system 102 may also be capable of acquiring positron emission tomography (PET) image data, or coincidence imaging. In this example, the CT imaging system 104 is high resolution, that is, the system 104 is capable of acquiring some or all of the same types of scan data as a diagnostic CT system (not shown). It should be understood that the multi-modality imaging system 100 may have other combinations of imaging systems, such that each of the imaging systems may be one of an NM imaging system, a CT imaging system, a PET imaging system, an X-ray imaging system (such as a C-arm, for example), a Magnetic Resonance Imaging (MRI) system, or other type of imaging system.

The NM and CT imaging systems 102 and 104 are both slidingly mounted on one or more rails 110 or other transporter, and are aligned so that the isocenters of the two imaging systems 102 and 104 are substantially collinear. In the illustrated embodiment, there is a set or pair of generally parallel rails 110, although any other number of rails may be used. Although not so limited, the imaging systems 102 and 104 may be provided with grooves in which the one or more rails 110 sit. Alternatively, the imaging systems 102 and 104 may be provided with one or more elongated rail-like protrusions that slide in female tracks of the rails 110. Wheels, ball bearings, and/or one or more drive screw may also be used to facilitate moving the NM and CT imaging systems 102 and 104 along the rails 110. Also, each of the NM and CT imaging systems 102 and 104 may have an associated drive motor (not shown) for driving the system along the rails 110.

A bed or table 106 is provided with a pallet 108. The table 106 is aligned with respect to the rails 110 and has a base that is fixed to the floor, such as by a pin, at the end furthest from the imaging systems 102 and 104. In one embodiment, the NM imaging system 102 is mounted on the rails 110 closer to the table 106 than the CT imaging system 104. A patient (not shown) lies on the pallet 108 and the pallet 108 is extended and/or driven through the NM imaging system 102 and the CT imaging system 104. The pallet 108 is illustrated in the fully extended position. By way of example only, the pallet 108 may accommodate a patient who is up to two meters tall, although other pallet and table lengths may be used and are not so limited. Therefore, the pallet 108 may be driven or extended for approximately six feet of travel. The table 106 may also be driven vertically to position a patient for scanning and to facilitate loading and unloading the patient.

The movement of the imaging systems 102 and 104 may be initiated automatically, such as by a particular protocol, or may be accomplished using user input controls, such as by holding a button or switch. Also, particular imaging positions may be predetermined such that the NM and CT imaging systems 102 and 104 may be automatically positioned at desired locations, such as by using sensors (e.g. optical, laser, and the like) and/or encoders. Therefore, the positioning of each of the NM and CT imaging systems 102 and 104 is precise for positioning to within a predetermined distance, such as, for example, 0.5 millimeter, of a desired position. Other tolerances may be used. This exact positioning allows image data from the two systems 102 and 104 to be registered with respect to each other.

The NM imaging system 102 has one or more detectors 112. In one embodiment, two detectors 112 are mounted on gantry 114 and may be positioned opposite each other. The detectors 112 may also be moved to other orientations. The detectors 112 each have a field of view (FOV) 174 corresponding to a face (not shown) of the detector 112. A display 128 is mounted to the gantry 114. An arm 130 extends from the gantry 114 to hold a remote control 132 and/or to provide user interface controls. Stator 134 is interconnected with the gantry 114 and mounted on (or otherwise interfaces with) the rails 110.

The diagnostic CT imaging system 104 may have an X-ray tube (not shown) having, for example, 20 Kilo Watts of power. This requires thick wires and/or cables and air conditioning to cool the X-ray tube. The CT imaging system 104 has a FOV 176 that is generally indicated as a line or plane corresponding to the position of the X-ray tube. In one embodiment, the FOV 176 may be, for example, 1.15 meters from a closest edge 178 of the FOV 174. The X-ray tube is rotated quickly, such as at 300 revolutions per minute (rpm), and thus the CT imaging system 104 needs to be stable and supported by a gantry. The CT imaging system 104 also has a stator 164 that is mounted on or interfaces with the rails. In other embodiments, other portions or apparatus associated with each of the NM and CT imaging systems 102 and 104 may be used to mount the imaging systems 102 and 104 separately on the rails 110.

As illustrated in FIG. 1, the CT imaging system 104 is positioned at an outer end 118 of the rails 110, that is, to the furthest extent away from, or as far as possible from, the table 106. The NM imaging system 102 is positioned proximate to the CT imaging system 104. In one embodiment, the NM and CT imaging systems 102 and 104 may be positioned to within, for example, 0.1 meter of each other as indicated by lines 166 and 168.

With the NM and CT imaging systems 102 and 104 positioned away from the table 106 as shown, the detectors 112 may be rotated about the pallet 108 to acquire image data. Also, the pallet 108 may be driven through the NM imaging system 102 to acquire image data over NM scan range 116 that extends between lines 144 and 146. The NM scan range 116 is based on the length of the rails 110 as well as the length of the pallet 108. In one example, the NM scan range 116 may be, for example, two meters. For example, the pallet 108 may be initially positioned such that a first anatomy of interest is positioned between the detectors 112 within the FOV 174 and towards an outer edge (not shown) of the pallet 108, such that scanning begins proximate line 144. The pallet 108 is then driven slowly in the direction of arrow A through the NM imaging system 102 while the detectors 112 acquire image data. Alternatively, the pallet 108 may be positioned and driven in the direction of arrow B while scanning.

In some embodiments, a pallet support 124 may be used to support the weight of the pallet 108 and the patient to prevent sag as the pallet 108 is extended. The pallet support 124 may have rollers or otherwise be configured to allow the pallet 108 to smoothly travel along the pallet support 124. By way of example only, the pallet support 124 may allow the pallet 108 to be made thinner or of lighter weight materials, or to increase the weight limit of the pallet 108.

When fully extended, the outer edge of the pallet 108 may not extend beyond an outer end 118 of the rails 110. Therefore, a footprint 122 of the system 100 is measured from an outer end 120 of the table 106 to an outer end 118 of the rails 110 or an outer edge 204 of the CT imaging system 104 when the CT imaging system 104 is at the furthest travel position, whichever is greater. In one embodiment, the footprint 122 of the system 100 may be, for example, 5.2 meters.

Figure 2:
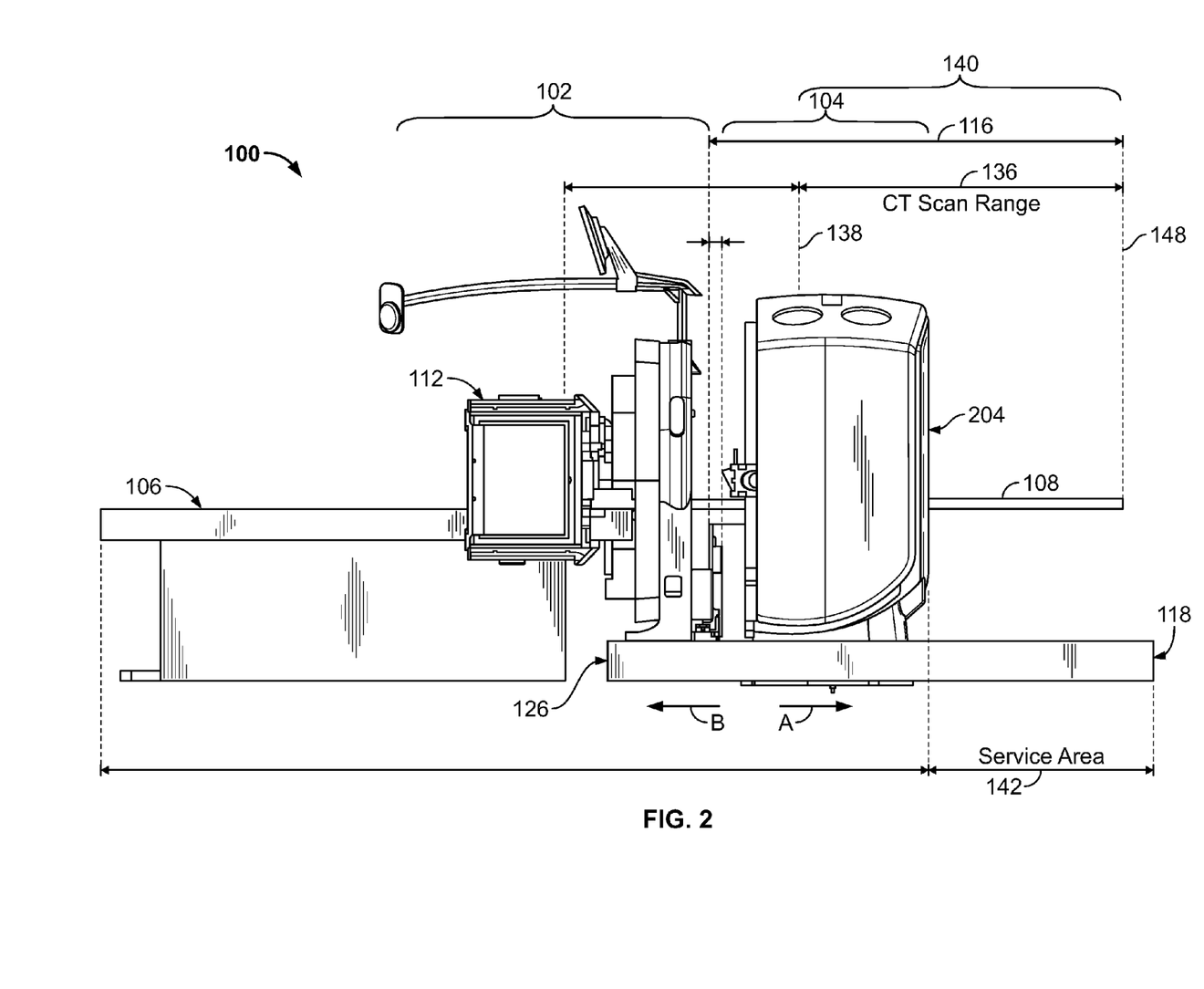
FIG. 2 illustrates the system of FIG. 1 wherein the NM and CT imaging systems are moved to an inner end of the rails in accordance with an embodiment of the present invention.

FIG. 2 illustrates the system 100 wherein the NM and CT imaging systems 102 and 104 have been moved to an inner end 126 of the rails 110. The detectors 112 are positioned in a vertical configuration on either side of the table 106 and are positioned out away from the table 106. In this position, the table 106 may fit between the detectors 112 and the detectors 112 cannot rotate around the pallet 108. The pallet 108 is again shown in the fully extended position.

By moving the NM imaging system 102 to the inner end 126 of the rails 110 and moving the CT imaging system 104 proximate to the NM imaging system 102, such as to within, for example, 0.1 meter of each other, CT scan range 136 between lines 138 and 148 may be maximized. In one embodiment, the CT scan range 136 may be, for example, 1.6 meters. For example, the patient may be positioned on the pallet 108. A portion of the patient to be scanned is positioned within the CT imaging system 104. The line 138 indicates the position within the CT imaging system 104 where scan planes are formed, or the FOV 176 as shown in FIG. 1. The pallet 108 is then driven in the direction of arrow A while the CT imaging system 104 acquires image data. Alternatively, the pallet 108 may be positioned and driven in the direction of arrow B. In some embodiments, when acquiring attenuation data the CT imaging system 104 may scan less of the patient compared to the NM imaging system 102. For example, the CT imaging system 104 may scan only the areas of expected high concentration of NM radiation collection to minimize the X-ray exposure to the patient. In other embodiments, the CT imaging system 104 may acquire image data over a portion or all of the CT scan range 136.

The NM and CT scan ranges 116 and 136 have an overlapping portion 140. In the overlapping portion 140, the pallet 108, and thus the anatomy of the patient, is in the same position with respect to the table 106 for both of the NM and CT acquisitions. Therefore, the pallet 108 has the same amount of sag at the same positions in both of the data sets acquired by the NM and CT imaging systems 102 and 104 within the overlapping portion 140. Any image data acquired within the overlapping portion 140 may be easily registered as no vertical alignment in needed.

In prior art systems having multi-modality systems aligned with respect to each other and fixed next to each other to the floor, the scan ranges are consecutive. The pallet of the table has to be long enough to travel linearly through each of the scan ranges. Therefore, extra space beyond the system positioned furthest from the table needs to be available to accommodate the extent of the pallet as the patient is moved through the outer scan range. In contrast, because the NM and CT imaging systems 102 and 104 are movable along the rails 110, the respective scan ranges 116 and 136 may overlap at least somewhat and less space around the systems 102 and 104 is needed.

Service area 142 provides room for personnel to service the CT imaging system 104. The service area 142 may be, for example, 1.1 meters, measured from the outer edge 204 of the CT imaging system 104 to the outer end 118 of the rails 110. Therefore, the outer end 118 of the rails 110 may be positioned proximate to a wall without compromising the service area 142.

Figure 3:
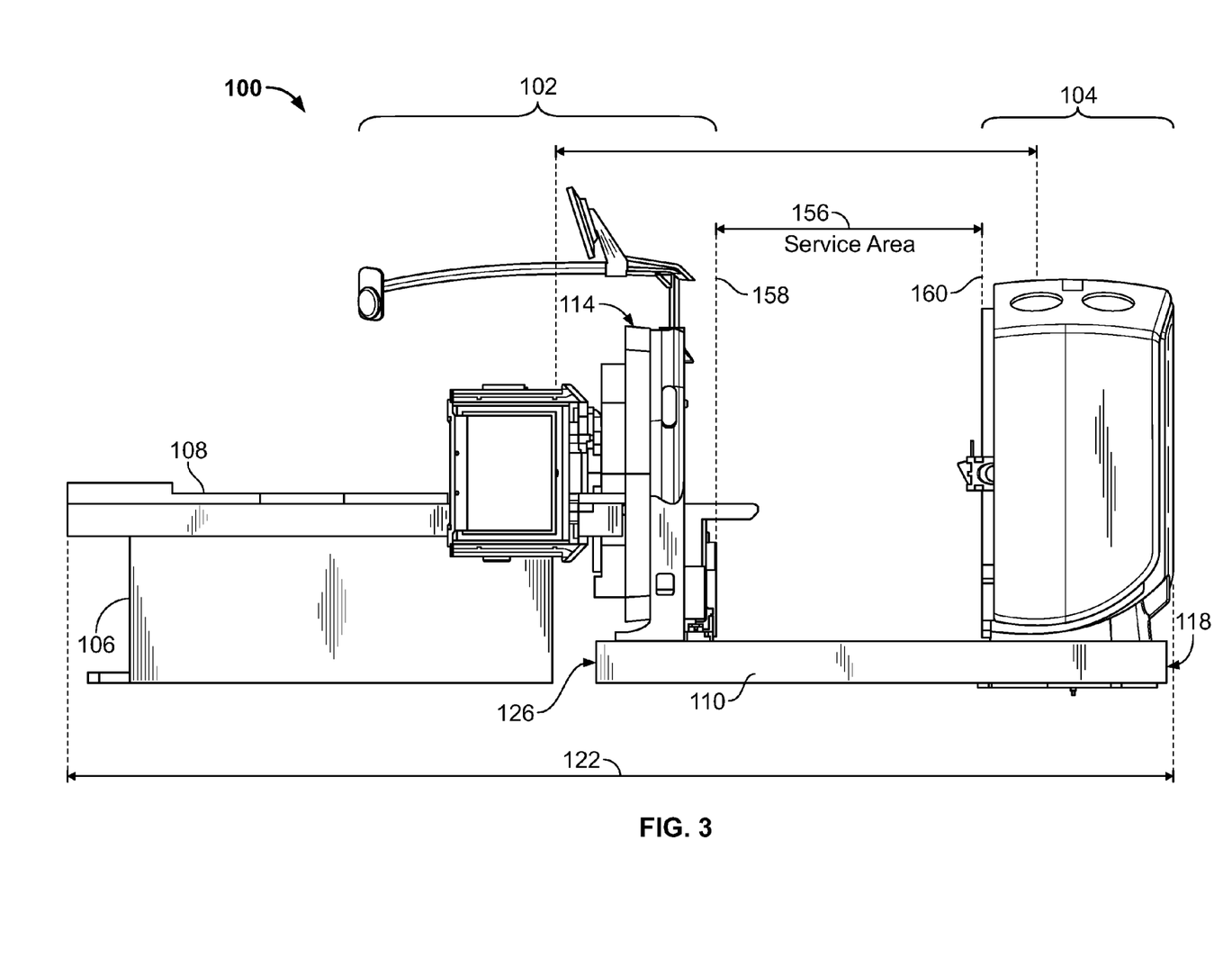
FIG. 3 illustrates positioning the NM and CT imaging systems at opposite ends of the rails to allow servicing in accordance with an embodiment of the present invention.

FIG. 3 illustrates positioning the NM and CT imaging systems 102 and 104 at opposite ends of the rails 110 to allow servicing of the back of the gantry 114 and the front of the CT imaging system 104. The pallet 108 of the table 106 is shown in the fully retracted position. The NM imaging system 102 is positioned proximate to the inner end 126 of the rails 110 and the CT imaging system 104 is positioned proximate to the outer end 118 of the rails 110. A service area 156 is thus available between the two imaging systems 102 and 104. In one embodiment, the service area 156 may be, for example, 1.3 meters, indicated by lines 158 and 160.

It should be understood that the service area 142 of FIG. 2 and the service area 156 may vary, depending on the size of each of the imaging systems 102 and 104 and the length of the rails 110. Additionally, the NM and CT scan ranges 116 and 136 may vary depending on the sizes of the imaging systems 102 and 104, the length of the rails 110, as well as the length of the pallet 108. For example, increasing the length of the rails 110 or the length of the pallet 108 may increase one or both of the NM and CT scan ranges 116 and 136. However, a larger footprint 122 would be created.

Figure 4:
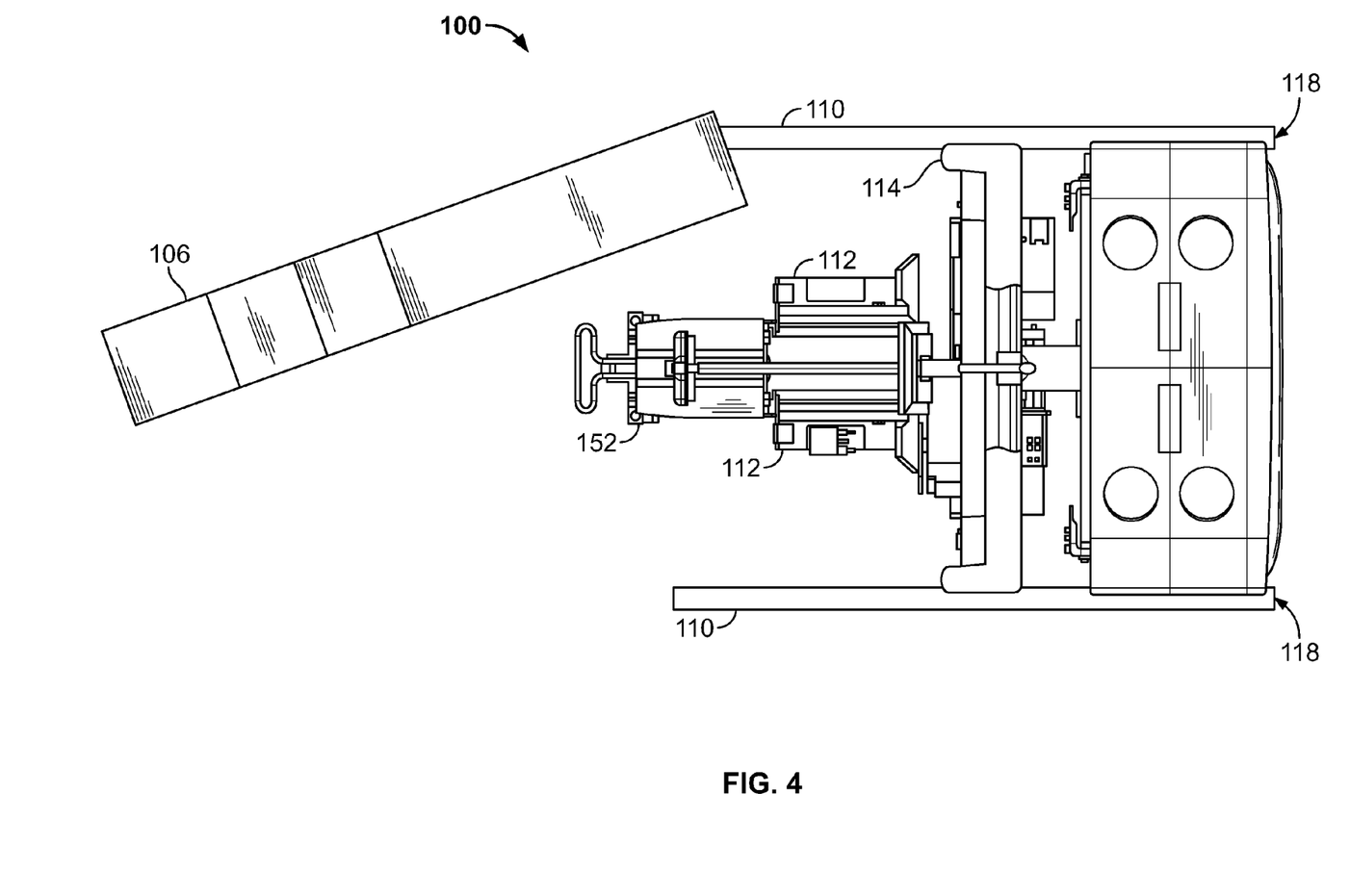
FIG. 4 illustrates a top view of the system of FIG. 1 with the table rotated away from the imaging systems in accordance with an embodiment of the present invention.
Figure 5:
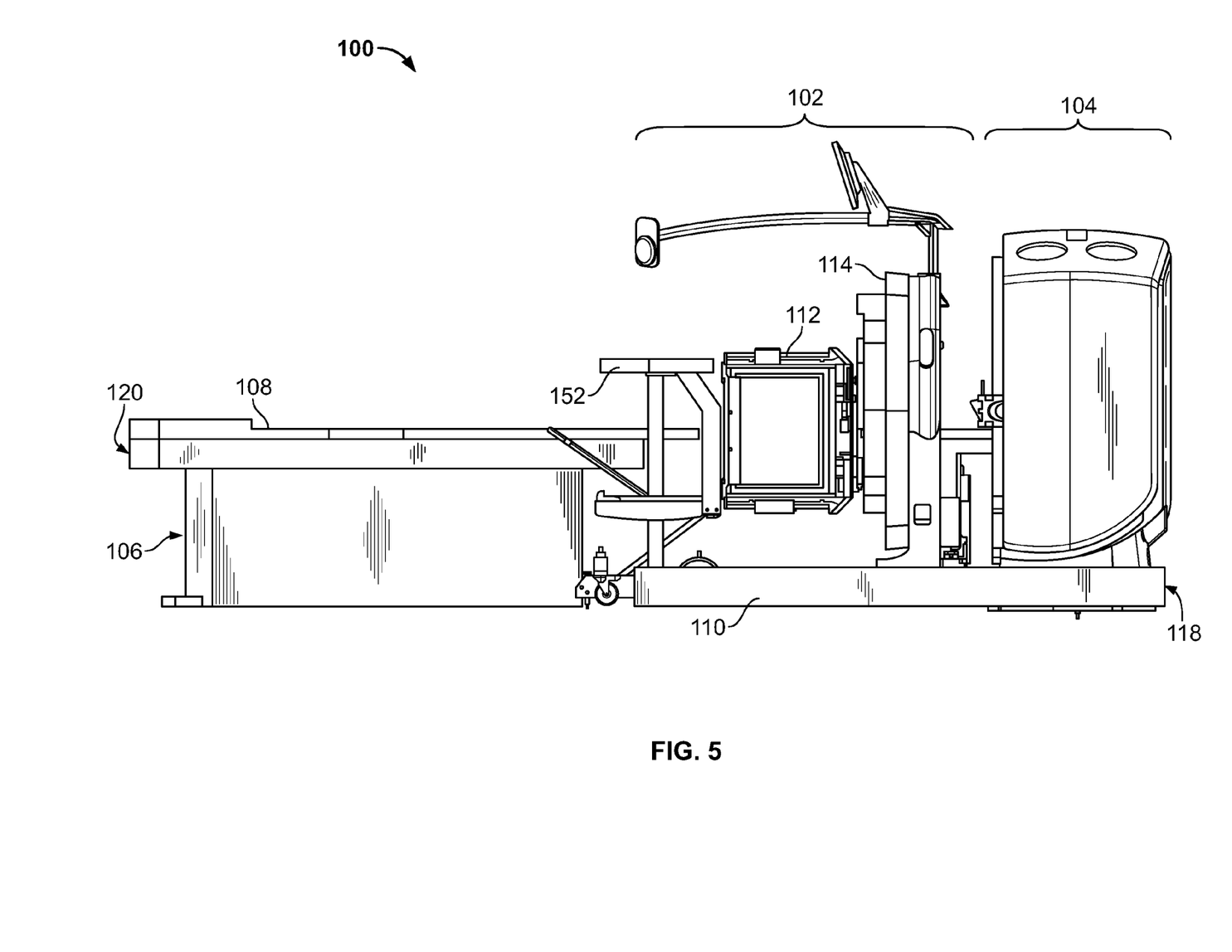
FIG. 5 illustrates a side view of the system of FIG. 1 with the table rotated away from the imaging systems in accordance with an embodiment of the present invention.

FIGS. 4 and 5 illustrate top and side views, respectively, of the system 100 with the table 106 rotated away from the NM and CT imaging systems 102 and 104. The NM and CT imaging systems 102 and 104 may be positioned on the rails 110 as far as possible from the table 106. The pallet 108 is fully retracted, or not extended away from the table 106. The table 106 may be pivoted or rotated, such as by 20 degrees, for example, towards one of the rails 110 and thus is no longer aligned with the rails 110. The detectors 112 may then be accessed with a collimator exchange cart 152. Each of the two detectors 112 has a collimator mounted to the face of the detector 112, and a single collimator exchange cart 152 holds both of the collimators. A different collimator exchange cart (not shown) may hold a different set of collimators suitable for different types of NM imaging. Also, by pivoting the table 106, more room is available for servicing the detectors 112 and the front side of the gantry 114 of the NM imaging system 102.

Figure 6:
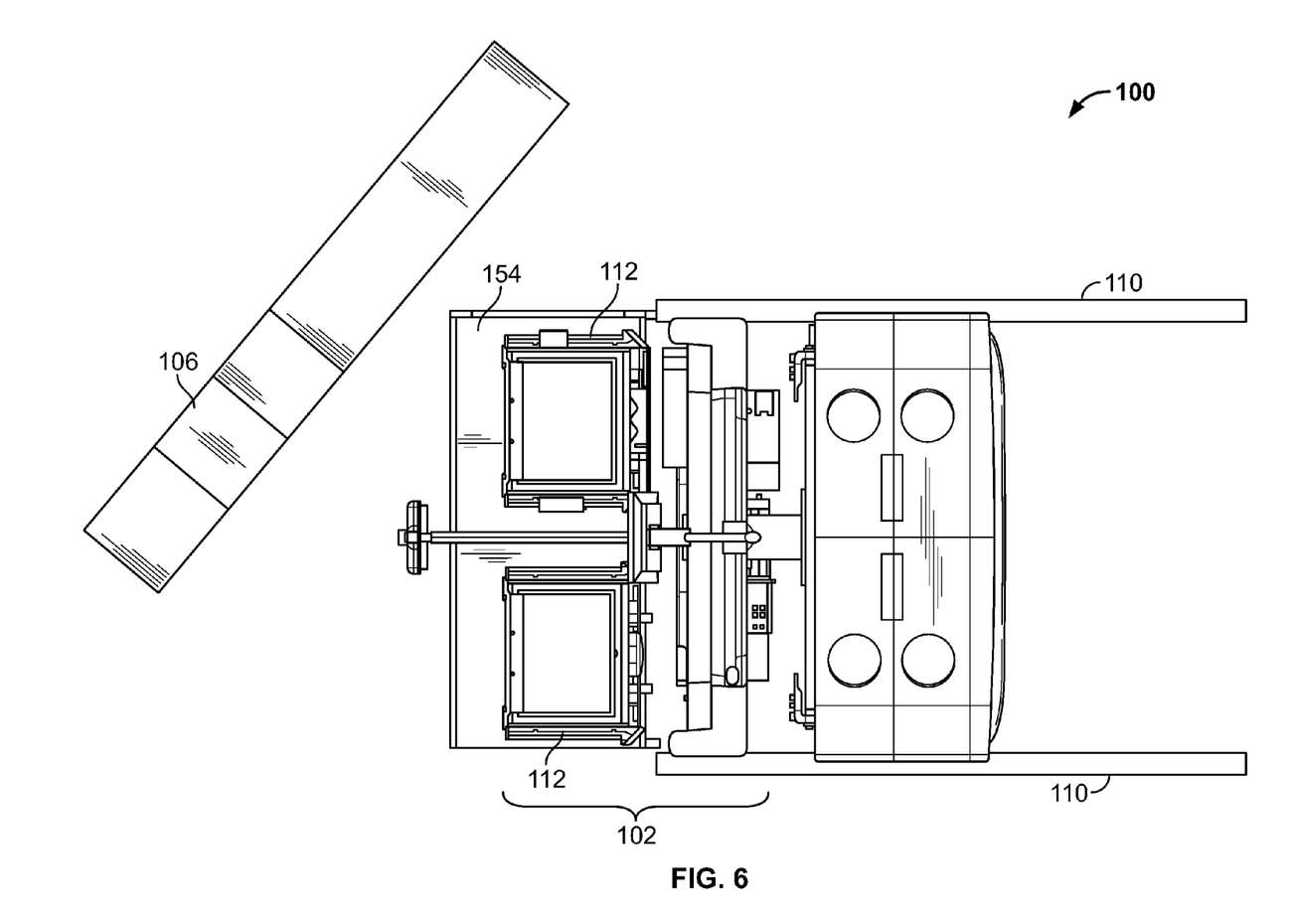
FIG. 6 illustrates using a separate stretcher or bed to image a patient with one of the imaging systems in accordance with an embodiment of the present invention.

FIG. 6 illustrates using a separate stretcher or bed 154 to image a patient with the NM imaging system 102. The table 106 is pivoted in the direction of the one of the rails 110 as needed, such as by 50 degrees or more, and may be pivoted up to 90 degrees. The detectors 112 are rotated such that the collimators are facing down towards the bed 154. Therefore, a patient (not shown) may be imaged without having to move the patient onto the pallet 108.

Figure 7:
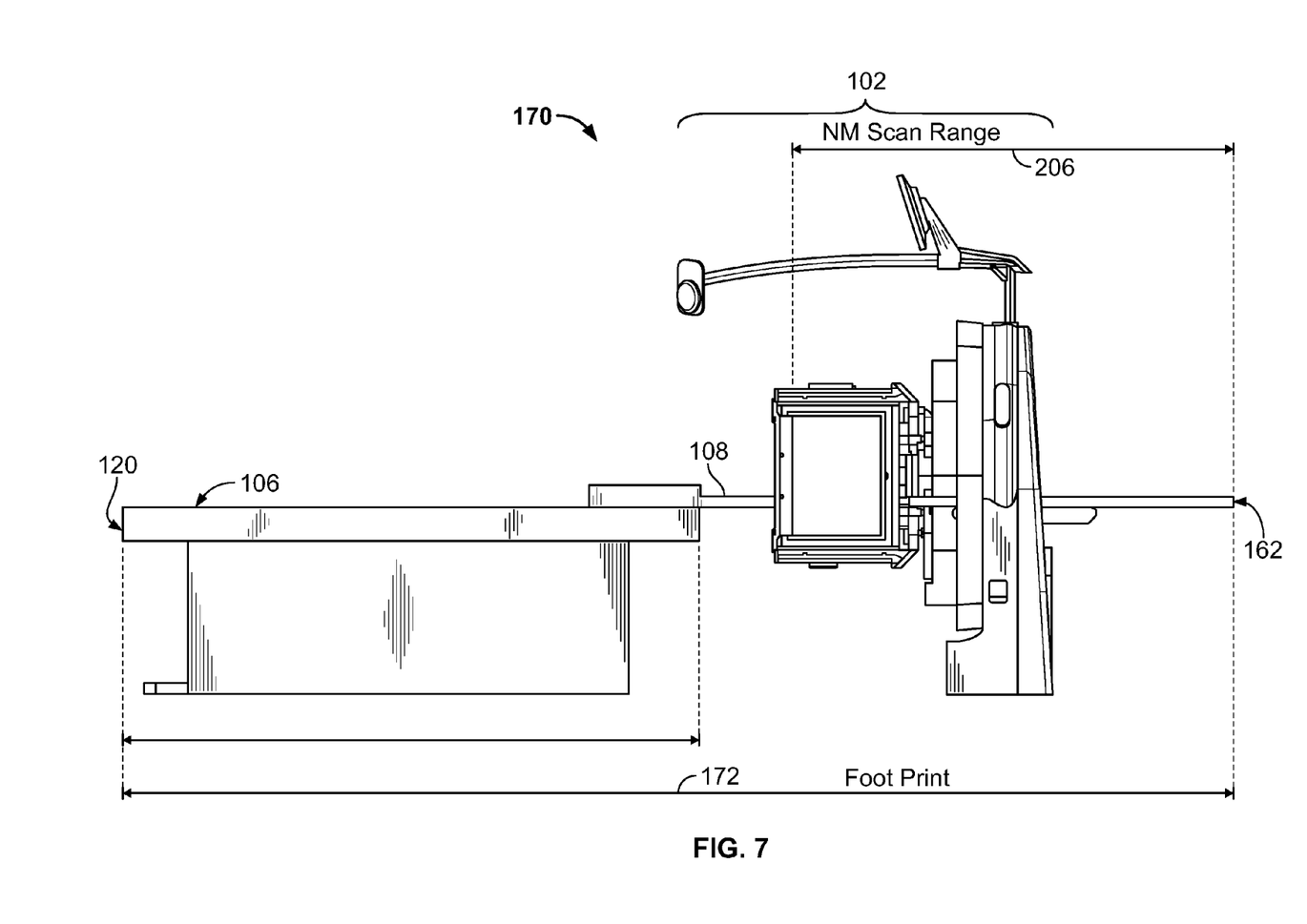
FIG. 7 illustrates an example of a general purpose (GP) configuration wherein an NM imaging system is fixed to the floor of a room.

FIG. 7 illustrates an example of a general purpose (GP) configuration 170 wherein the NM imaging system 102 is fixed to the floor of the room. As shown, no CT imaging system is installed. The table 106 may be 2.6 meters, for example, and the foot print 172 of the configuration 170 may be 5 meters, measured from the outer end 120 of the table 106 to an outer end 162 of the pallet 108 when the pallet 108 is fully extended. An NM scan range 206 of two meters is indicated. If a CT or other imaging system were mounted to the floor and integrated into the configuration 170, the pallet 108 would need to have an extended length to provide the desired CT scan range as discussed previously. Also, the room needed to accommodate the combined systems would increase as the footprint 172 increases.

Figure 8:
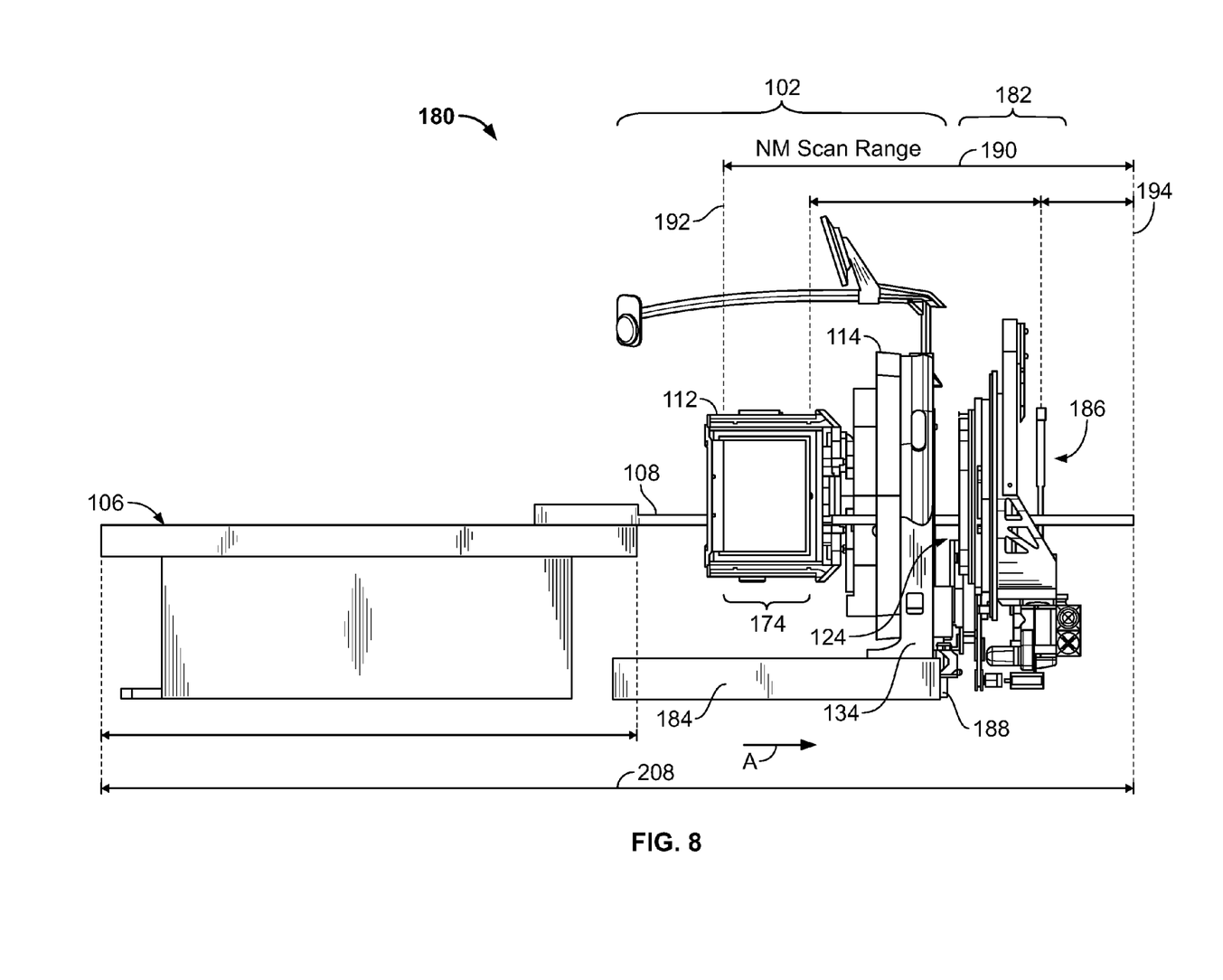
FIG. 8 illustrates another multi-modality imaging system formed in accordance with an embodiment of the present invention.

FIG. 8 illustrates multi-modality imaging system 180 having the NM imaging system 102 and a CT imaging system 182. In contrast with the CT imaging system 104 of FIG. 1, the CT imaging system 182 is not a full diagnostic CT system having detailed resolution. Instead, the CT imaging system 182 is a lower cost system used primarily for attenuation correction of the NM image data, anatomical registration and lower resolution imaging. For example, the CT imaging system 182 may have an X-ray tube (not shown) having approximately 200 Watts of power. The cooling needed is much less in comparison to the CT imaging system 104, and the X-ray tube is rotated much slower, such as at approximately 5-10 rpm. Therefore, the CT imaging system 182 may be much smaller than the CT imaging system 104. In one embodiment, the CT imaging system 182 may not have a dedicated gantry, but may instead be mounted to and rotated about the gantry 114 of the NM imaging system 102.

The stator 134 of the NM imaging system 102 is mounted on one or more rails 184 or transporter for moving the system 180. The rails 184 may be shorter in length than the rails 110 because the CT imaging system 182 is smaller. The CT imaging system 182 extends out away from the rails 184 and is not connected to the rails 184. Instead, the CT imaging system 182 is mounted to the stator 134, the gantry 114 and/or other component of the imaging system 102. The CT imaging system 182 acts as a counter-balance to the weight of the detectors 112. In one embodiment, the GP configuration 170 of FIG. 7 may be modified or retrofitted with the CT imaging system 182 and the rails 184 without creating a larger footprint 172.

The CT imaging system 182 is configured so that servicing may be accomplished proximate a back end 186. Therefore, the NM and CT imaging systems 102 and 182 do not need to be separated for servicing. The system 180 has a foot print 208 that may be the same as the foot print 172 of the GP configuration 170 of FIG. 7.

When the system 180 is moved proximate outer end 188 of the rails 184, a patient may be scanned within NM scan range 190, extending from line 192 to line 194 as the pallet 108 is driven through the FOV 174, such as in the direction of arrow A. By way of example only, the NM scan range 190 may be two meters, or the same as the NM scan range 116 of the system 100. Optionally, the pallet support 124 may be used.

Figure 9:
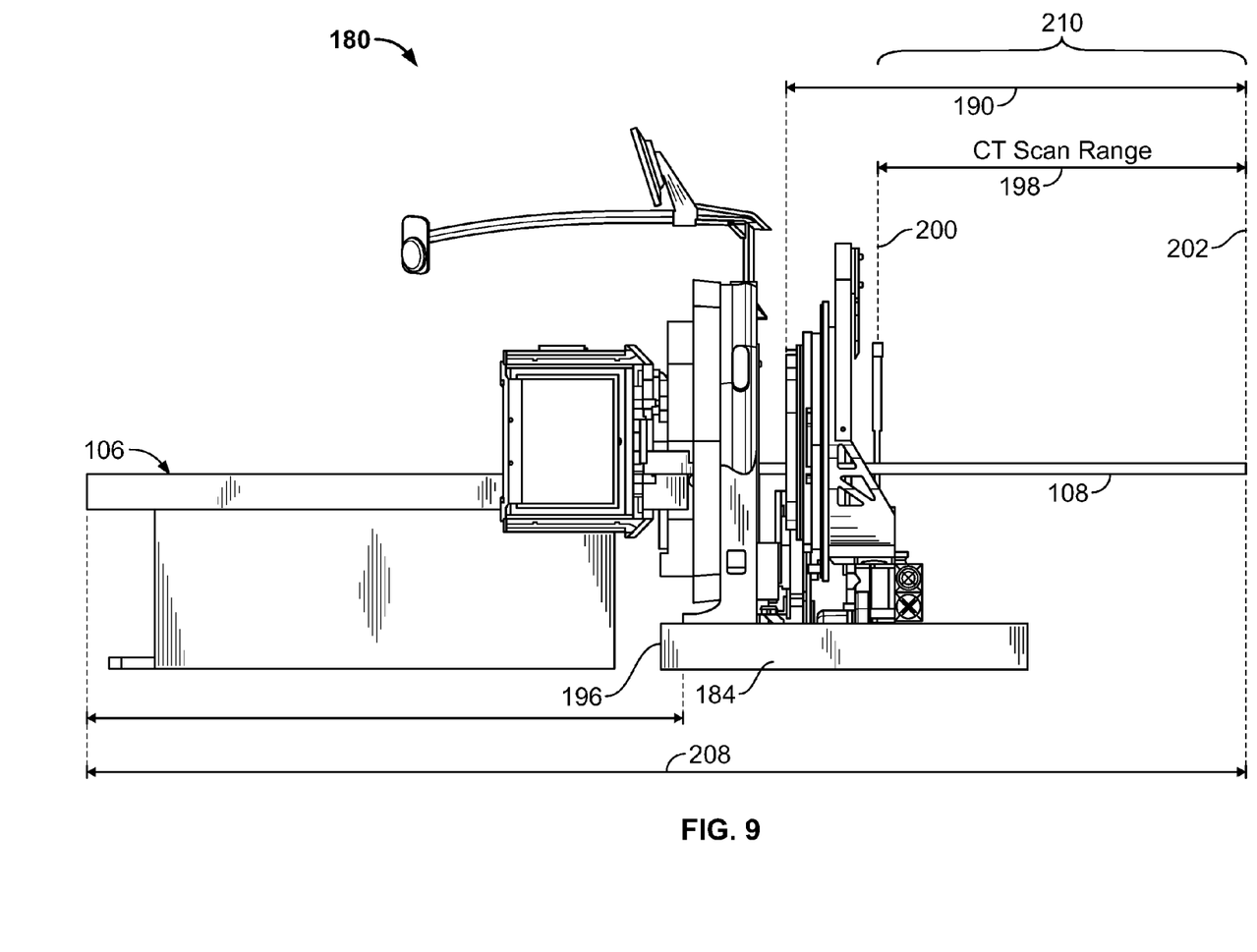
FIG. 9 illustrates moving the system of FIG. 8 to an inner end of the rails to extend the scan range of one of the imaging systems in accordance with an embodiment of the present invention.

FIG. 9 illustrates moving the system 180 to an inner end 196 of the rails 184 to extend CT scan range 198 from line 200 to line 202. The line 200 indicates the position within the CT imaging system 182 where the scan planes are formed or the FOV. The NM and CT scan ranges 190 and 198 have an overlapping portion 210 wherein the pallet 108, and thus the patient anatomy, is at the same position or distance from the table 106 for both acquisitions. Therefore, any sag experienced by the pallet 108 will be the same for both image data sets.

In another embodiment, referring to both of the systems 100 and 180, image data may be acquired when moving one or both of the imaging systems along the rails while either holding the pallet 108 stationary or moving the pallet 108 in the opposite direction.

Figure 10:
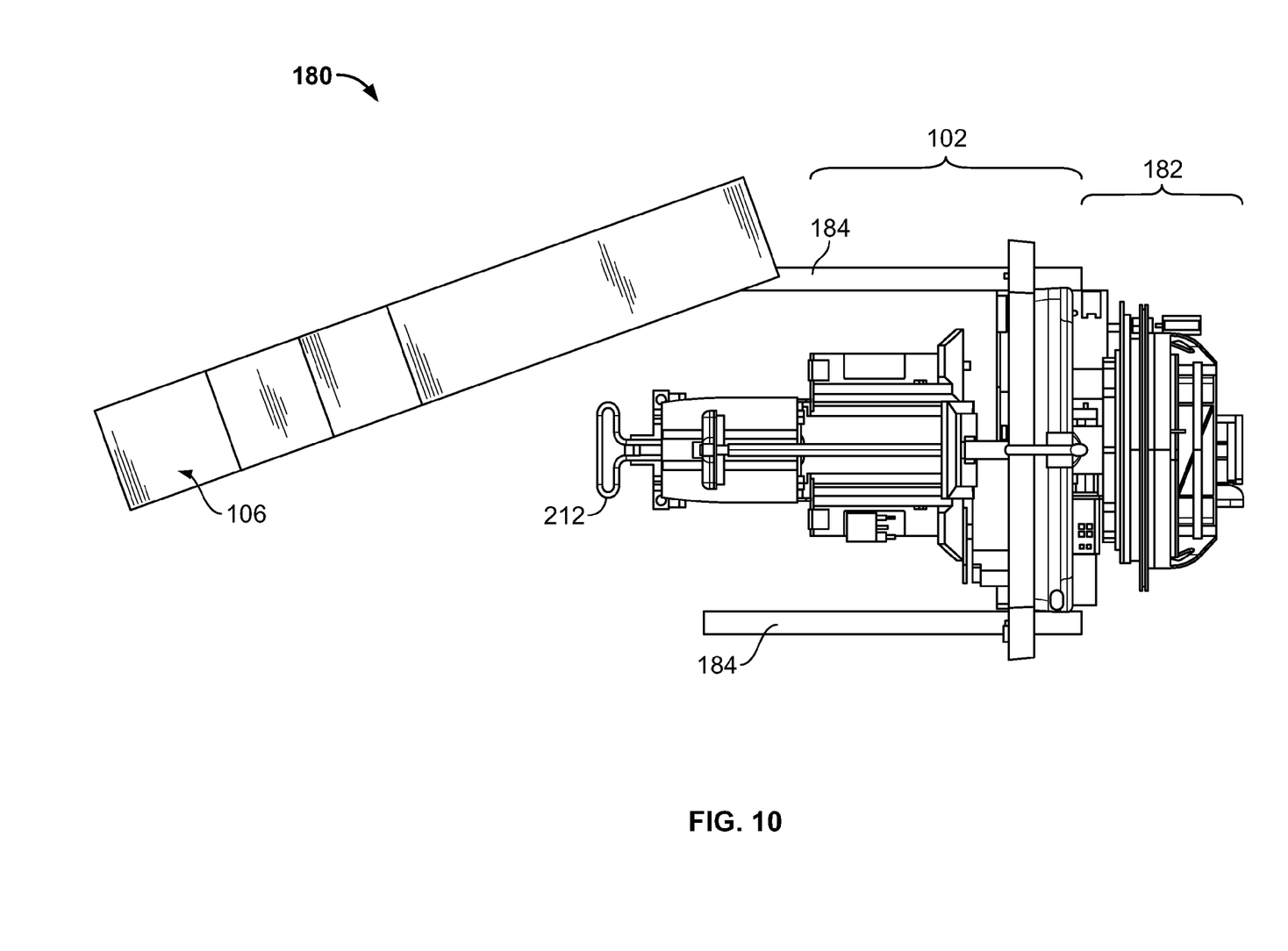
FIG. 10 illustrates the system of FIG. 8 having the table rotated towards one of the rails in accordance with an embodiment of the present invention.

FIG. 10 illustrates the system 180 having the table 106 rotated towards one of the rails 184. Two rails 184 are shown. Similar to FIG. 4, space is created for access with a collimator exchange cart 212. The table 106 may be further rotated so that an external bed (not shown) may be used as discussed in FIG. 6.

A technical effect of at least one embodiment is the ability to shorten the footprint of a multi-modality imaging system while providing desired scan ranges. Therefore, the effective scan range of the multi-modality imaging system may be increased while using a standard length pallet in a standard size room. The imaging systems are mounted on at least one rail or transport and are positioned proximate each other along the rail at positions relative to the table. The positions depend upon which imaging system is acquiring image data. The pallet is driven through the two imaging systems while acquiring image data. Therefore, more than one modality may be accommodated within a smaller room or space. The scan ranges of the two imaging systems have an overlapping portion, and thus any sag experienced by the pallet when the pallet is extended occurs at the same anatomical position of the patient in both of the scan ranges, significantly improving the registration between the two images.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A multi-modality imaging system comprising:
   a first imaging system;
   a second imaging system that is different from the first imaging system, the first and second imaging systems having different detector types;
   at least one rail upon which the first and second imaging systems are slidingly mounted; and
   a table comprising a movable pallet configured to extend through a scan range of the first imaging system while the first imaging system acquires data and while the first and second imaging systems are positioned proximate each other at one position along the at least one rail, the pallet further configured to extend through a scan range of the second imaging system while the second imaging system acquires data and while the first and second imaging systems are positioned proximate each other at a different position along the at least one rail, at least a portion of the scan ranges overlapping each other.

2. The system of claim 1, wherein the first and second imaging systems are one of a Nuclear Medicine (NM) imaging system, a Computed Tomography (CT) imaging system, a Positron Emission Tomography (PET) imaging system, an X-ray imaging system, and a Magnetic Resonance Imaging (MRI) system.

3. The system of claim 1, wherein both of the first and second imaging systems are configured to be slidingly mounted to the at least one rail.

4. The system of claim 1, wherein the first imaging system comprises a stator configured to be slidingly mounted to the at least one rail and wherein the second imaging system is configured to be mounted to the first imaging system.

5. The system of claim 1, wherein the first imaging system is configured to be closer to the table on the at least one rail than the second imaging system, wherein the first and second imaging systems are positioned at an outer end of the at least one rail with respect to the table when the first imaging system acquires image data, and wherein the first and second imaging systems are positioned at an inner end of the at least one rail with respect to the table when the second imaging system acquires image data.

6. The system of claim 1, wherein the first imaging system is slidingly mounted on the at least one rail and the second imaging system is mounted to a back side of the first imaging system, the first and second imaging systems moving together along the at least one rail.

7. The system of claim 1, wherein the table is configured to be aligned with the at least one rail, the table further configured to be rotatable away from the at least one rail.

8. The system of claim 1, further comprising at least one motor configured to drive at least one of the first and second imaging systems along the at least one rail.

9. The system of claim 1, wherein the scan ranges are based on a length of the at least one rail and a length of the pallet.

10. The system of claim 1, wherein a patient supported on the pallet is in a same position vertically, with respect to a floor on which the rail is mounted, for the scan ranges for both of the first and second imaging systems.

11. A method for using a multi-modality imaging system, comprising:
    positioning first and second imaging systems proximate each other along at least one rail at a location with respect to a table, the table having a pallet configured to extend through the first and second imaging systems;
    acquiring image data with at least one detector of the first imaging system that is physically separate from the second imaging system;
    positioning the first and second imaging systems proximate each other at a different location along the at least one rail that is closer to the table; and
    acquiring image data with the second imaging system, wherein at least a portion of the image data acquired by each of the first and second imaging systems is acquired at a same distance away from the table.

12. The method of claim 11, further comprising:
    driving the pallet a first time through at least a portion of a scan range while acquiring the image data with the first imaging system; and
    driving the pallet a second time through at least a portion of a scan range while acquiring the image data with the second imaging system, at least a portion of the scan ranges overlapping each other.

13. The method of claim 11, wherein the first imaging system acquires NM image data and the second imaging system acquires at least one of CT image data and CT attenuation data.

14. The method of claim 11, wherein the positioning further comprises driving the first and second imaging systems separately to the locations.

15. The method of claim 11, wherein the positioning further comprises driving the first and second imaging systems to within a predetermined distance of each other.

16. The method of claim 11, wherein the first imaging system is slidingly mounted on the at least one rail and the second imaging system is mounted to the first imaging system, the positioning further comprising driving the first and second imaging systems at the same time.

17. The method of claim 11, further comprising:
    detecting a location of at least one of the first and second imaging systems along the at least one rail; and
    driving the at least one of the first and second imaging systems to a predetermined location along the at least one rail.

18. The method of claim 11, further comprising:
    separating the first and second imaging systems from each other by positioning each of the imaging systems at opposite ends of the at least one rail; and
    servicing at least one of the imaging systems after separating them from each other.

19. A multi-modality imaging system, comprising:
    a first imaging system;
    a second imaging system that is different from the first imaging system, the second imaging system mounted to the first imaging system proximate a back end of the first imaging system;
    at least one rail upon which the first imaging system is slidingly mounted, the second imaging system not slidingly mounted on the at least one rail, and the first and second imaging systems being movable along the at least one rail; and
    a table comprising a movable pallet configured to extend through a scan range of the first imaging system while the first imaging system is positioned proximate an outer end of the at least one rail, the pallet further configured to extend through a scan range of the second imaging system while the first imaging system is positioned proximate an inner end of the at least one rail, at least a portion of the scan ranges overlapping each other.

20. The system of claim 19, wherein the first imaging system is a NM imaging system and the second imaging system is a low resolution CT imaging system.

* * * * *